US010111777B2

United States Patent
Gunn (10) Patent No.: US 10,111,777 B2
(45) Date of Patent: Oct. 30, 2018

(54) TRACTION-LIMITING VITRECETOMY PROBE

(71) Applicant: Novartis AG, Basel (CH)

(72) Inventor: Nicholas Max Gunn, Newport Beach, CA (US)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 14/549,356

(22) Filed: Nov. 20, 2014

(65) Prior Publication Data

US 2016/0143780 A1     May 26, 2016

(51) Int. Cl.
    *A61F 9/007*            (2006.01)
    *A61B 17/32*            (2006.01)
    *A61B 17/00*            (2006.01)
    *A61B 17/3207*        (2006.01)

(52) U.S. Cl.
CPC .... *A61F 9/00763* (2013.01); *A61B 17/32002* (2013.01); *A61B 17/320783* (2013.01); *A61B 2017/00544* (2013.01); *A61B 2017/320028* (2013.01); *A61B 2017/320032* (2013.01); *A61F 9/00736* (2013.01)

(58) Field of Classification Search
CPC .. A61F 9/00736; A61F 9/00763; A61B 17/32; A61B 17/32002; A61B 17/320016; A61B 17/320783; A61B 17/3207; A61B 17/3205; A61B 2017/320024; A61B 2017/320028; A61B 2017/320032; A61B 2017/32004; A61B 2017/320064; A61B 2017/00544
See application file for complete search history.

(56) References Cited

U.S. PATENT DOCUMENTS

| | | | |
|---|---|---|---|
| 4,203,444 A * | 5/1980 | Bonnell | A61B 17/32002 600/565 |
| 5,395,313 A * | 3/1995 | Naves | A61B 17/1608 600/564 |
| 5,403,276 A * | 4/1995 | Schechter | A61B 17/32002 604/118 |
| 5,409,013 A * | 4/1995 | Clement | A61B 10/04 600/566 |
| 8,545,529 B2 * | 10/2013 | Underwood | A61B 17/32002 604/22 |
| 2008/0172077 A1 * | 7/2008 | Valencia | A61F 9/00763 606/170 |
| 2008/0172078 A1 * | 7/2008 | Svetic | A61B 17/320783 606/171 |
| 2010/0191178 A1 * | 7/2010 | Ross | A61F 9/00736 604/22 |
| 2012/0157906 A1 * | 6/2012 | Underwood | A61B 17/32002 604/22 |
| 2012/0157907 A1 * | 6/2012 | Underwood | A61B 17/32002 604/22 |

(Continued)

*Primary Examiner* — Christopher L Templeton (57) ABSTRACT

Apparatuses, systems, and methods are described for selectively generating an aspiration flow within a surgical instrument. Particularly, the disclosure describes example vitrectomy probes operable to selectively generate an aspiration flow in relation to operation of the cutter of the vitrectomy probe. In some instances, one or more valves may be used to form a barrier or closure and create a piston effect in order to selectively generate an aspiration flow.

7 Claims, 5 Drawing Sheets

(56) References Cited

U.S. PATENT DOCUMENTS

| | | | |
|---|---|---|---|
| 2012/0157908 A1* | 6/2012 | Underwood | A61B 17/32002 604/22 |
| 2012/0157909 A1* | 6/2012 | Underwood | A61B 17/32002 604/22 |
| 2012/0158029 A1* | 6/2012 | Underwood | A61B 17/32002 606/171 |
| 2012/0158030 A1* | 6/2012 | Underwood | A61B 17/32002 606/171 |
| 2013/0053759 A1* | 2/2013 | McCawley | A61F 9/00763 604/22 |
| 2015/0105791 A1* | 4/2015 | Truckai | A61B 17/320068 606/115 |
| 2015/0190163 A1* | 7/2015 | Ciulla | A61B 17/32002 606/115 |

\* cited by examiner

TRACTION-LIMITING VITRECETOMY PROBE

TECHNICAL FIELD

The present disclosure relates to systems, apparatuses, and methods for traction-limiting vitrectomy probes. Particularly, this disclose relates to systems, apparatuses, and methods for vitrectomy probes having one or more internal valves to create a displacement pump and reduce or eliminate traction on the retina of an eye.

BACKGROUND

Vitrectomy probes are used during vitreoretinal surgery to remove ocular tissues, such as vitreous humor and membranes covering the retina. These probes generally include a port for drawing in and dissecting tissues. The port opens, tissue is drawn into the port, the port closes, severing the tissue, and the tissue is aspirated. This action may be repeated to remove desired tissues.

SUMMARY

According to one aspect, the disclosure describes a surgical instrument that includes a body, a cutter coupled to the body, and a motor. The cutter may include an outer cutting member having a port and an inner cutting assembly. The inner cutting assembly may be slideable within the outer cutting member. The inner cutting assembly may include an inner cutting member; and a valve selectable between an open configuration and a closed configuration. The motor may be operable to reciprocate the inner cutting assembly between an extended position and a retracted position.

Another aspect of the disclosure encompasses a method of operating a surgical instrument. The method may include forming an occlusion within a portion of an inner cutting member; retracting the inner cutting member within an outer cutting member in a first direction; removing the occlusion within the portion of the inner cutting member; and extending the inner cutting member within an outer cutting member in a second direction opposite the first direction.

Another aspect of the disclosure encompasses a vitrectomy probe that may include a body and a cutter extending from the body. The cutter may include an outer cutting member and an inner cutting member slideable within the outer cutting member between an extended position and a retracted position. The vitrectomy probe may also include a diaphragm coupled to the inner cutting member and disposed within a chamber formed in the body. The diaphragm may divide the chamber into a first chamber portion and a second chamber portion. The diaphragm may be moveable in a first direction to retract the inner cutting member in response to a first pneumatic pressure introduced into the first chamber portion. The vitrectomy probe may also include a first valve coupled to the inner cutting member. At least a portion of the valve may be disposed in the first chamber portion and adapted to be closed upon introduction of the first pneumatic pressure into the first chamber portion.

The various aspects may include one or more of the following features. The valve may be configured to close when the inner cutting assembly is in the extended position. The valve may be configured to open when the interior cutting assembly is in the retracted position. The body may include a chamber, and the motor may be at least partially disposed in the chamber. The motor may include a diaphragm, and the diaphragm may be displaced into the retracted position by a first pneumatic pressure. The valve may be configured to close in response to the first pneumatic pressure. The valve may be configured to open upon removal of the first pneumatic pressure. The valve may include a tubular member defining an opening and a resilient member disposed on the tubular member and overlaying the opening.

The various aspects may include one or more of the following features. Forming an occlusion within a portion of an inner cutting member may include closing a valve coupled to the inner cutting member. Closing a valve coupled to an inner cutting member may include applying a pneumatic pressure to at least a portion of the valve. Removing the occlusion formed within a portion of an inner cutting member may include opening the valve coupled to the inner cutting member. Opening a valve coupled to an inner cutting member may include removing an applied pneumatic pressure from at least a portion of the valve. Retracting an inner cutting member within an outer cutting member in a first direction may include applying a pneumatic pressure to a side of a diaphragm coupled to the inner cutting member. Extending an inner cutting member within an outer cutting member in a second direction opposite the first direction may include applying a pneumatic pressure to a side of a diaphragm coupled to the inner cutting member.

The various aspects may also include one or more of the following features. An inner cutting assembly may include an inner cutting member, a tubular member, and a first valve. The inner cutting assembly may define a passageway therethrough. The first valve may be operable to form a closure within the passageway. A second valve may be disposed in the body adjacent to an end of the inner cutting assembly opposite the inner cutting member. The second valve may be adapted to close upon introduction of a second pneumatic pressure into the second chamber portion.

It is to be understood that both the foregoing general description and the following detailed description are exemplary and explanatory in nature and are intended to provide an understanding of the present disclosure without limiting the scope of the present disclosure. In that regard, additional aspects, features, and advantages of the present disclosure will be apparent to one skilled in the art from the following detailed description.

DETAILED DESCRIPTION

The present disclosure relates to systems, apparatuses, and methods to limit traction on a retina during vitreoretinal surgical procedures. Vitreous humor contained within an eye may be adhered to the retina. Traction generally results when the vitreous humor is pulled, such as during a vitrectomy procedure, and, consequently, the retina is pulled. This traction can lead to retinal injury, such as a retinal tear or detachment of a portion of the retina from the eye. In some instances, an example vitrectomy probe may include one or more valves to occlude a portion of an aspiration conduit and create a piston effect that can drive the movement of material. In some instances one or more valves may be used to occlude one or more portions of an aspiration conduit. The one or more valves may be selectively closed during a portion of movement of the vitrectomy probe. For example, the one or more valves may be closed during at least a portion of a stroke movement of a cutter of the vitrectomy probe. In some instances, the one or more valves may include a pneumatic pinch valve. However, any type of valve may be used.

Figure 1:
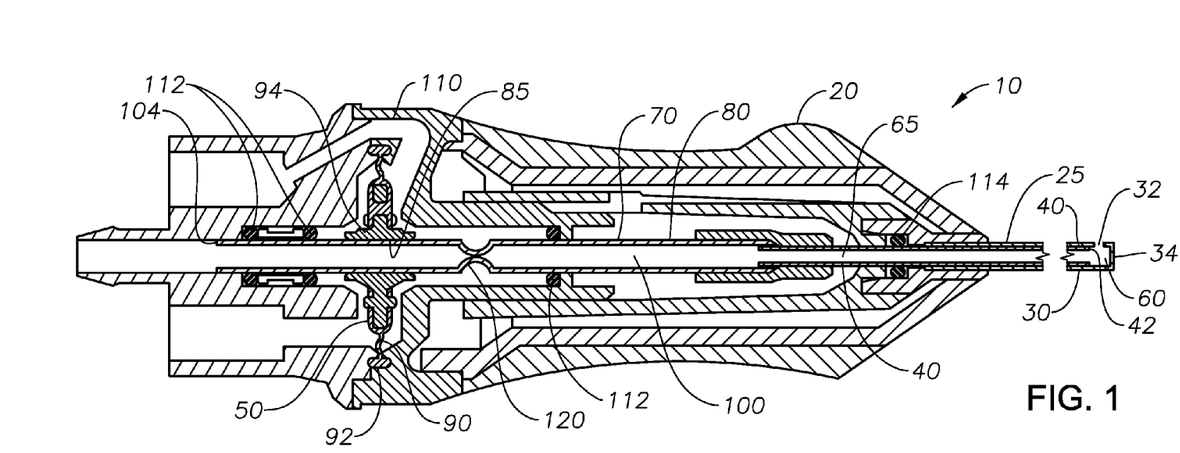
FIG. 1 is a cross-sectional view of an example vitrectomy probe.

FIG. 1 shows a cross-sectional view of an example vitrectomy probe 10 that includes a body 20, a cutter 25, and a motor 50. The cutter 25 may include an outer cutting member 30 and an inner cutting member 40. The inner cutting member 40 is slideable within a lumen 60 of the outer cutting member 30. The inner cutting member 40 may be tubular and define a lumen 65. The motor 50 is coupled to the inner cutting member 40. For example, the inner cutting member 40 may be coupled directly to the motor 50. In other instances, the inner cutting member 40 may form part of an inner cutting assembly 70. In some instances, the inner cutting assembly 70 may include a tubular member 80. The tubular member 80 may extend through a central opening 85 formed in the motor 50. In other instances, the inner cutting member 40 may extend through the central opening 85.

The remainder of the description will be made with reference to an implementation of the vitrectomy probe 10 that includes the inner cutting assembly 70 having the inner cutting member 40 and tubular member 80. However, it is understood that the scope of the disclosure is not so limited. Rather, the scope of the disclosure includes an inner cutting assembly that may include additional or different components than those described as well as implementations in which the inner cutting member 40 extends through the motor 50. Further, as also explained, implementations of vitrectomy probes within the scope of the disclosure may have an inner cutting member that does not form part of an inner cutting assembly but, rather, that extends from the outer cutting member 30 to the motor 50. As such, the following description is provided as a non-limiting example.

The inner cutting assembly 70 defines a passageway 100 extending from a distal end 34 of the outer cutting member 30 to a proximal end 104 of the inner cutting assembly 70. Thus, the passageway 100 includes the lumen 65 of the inner cutting member 40. Additionally, the volume of the passageway 100 effectively increases and decreases as the inner cutting member 40 is retracted and extended relative to the outer cutting member 30. The passageway 100 is operable to conduct aspirated materials through the vitrectomy probe 10. The outer cutting member 30 defines a port 32 at the distal end 34 of the outer cutting member 30. The port 32 communicates with the lumen 60. The inner cutting member 40 includes a distal end 42. As the inner cutting member 40 reciprocates within the outer cutting member 30, the distal end 42 passes by the port 32 and severs material entering therethrough. The severed material is aspirated though lumen 60 and passageway 100 and, ultimately, out of the vitrectomy probe 10.

In some instances, the motor 50 may be a pneumatically-actuated motor. For example, in some instances, the motor 50 may include a diaphragm 90 disposed in a chamber 110 formed in the body 20. In some instances, an outer periphery 92 of the diaphragm 90 may be coupled to the body 20, and an inner periphery 94 of the diaphragm 90 may be coupled to the inner cutting assembly 70. Seals 112 may be disposed in the chamber 110. In some instances, one or more of the seals 112 may provide an air-tight seal. The seals 112 may serve to center the inner cutting assembly 70 within chamber 110. The vitrectomy probe 10 may also include a seal 114 between the inner cutting assembly 70 and the body 20. The seal 114 may also serve to align the inner cutting assembly 70 within the body 20. In some instances, the seal 114 may provide an air-tight seal.

The diaphragm 90 may be oscillated by alternately applying pneumatic pressure to opposite sides of the diaphragm 90, thereby oscillating the inner cutting member 40 within the outer cutting member 30. This type of motor may be described as a double-action motor. In some instances, a single-action motor may be used. For example, the vitrectomy probe 10 may include a return spring, or other type of biasing member, disposed between the diaphragm 90 and the housing 20 in the chamber 110. Pneumatic pressure may be applied to a side of the diaphragm 90, opposite the spring. The pneumatic pressure displaces the diaphragm 90 in a first direction, compressing the spring. Upon removal of the pneumatic pressure, the diaphragm 90 is biased and displaced in a direction opposite the first direction. However, the motor 50 may be any type of device operable to oscillate the inner cutting member 40. For example, the motor may be an electric motor, hydraulic, piezoelectric, or any other type of motor.

Figure 2:
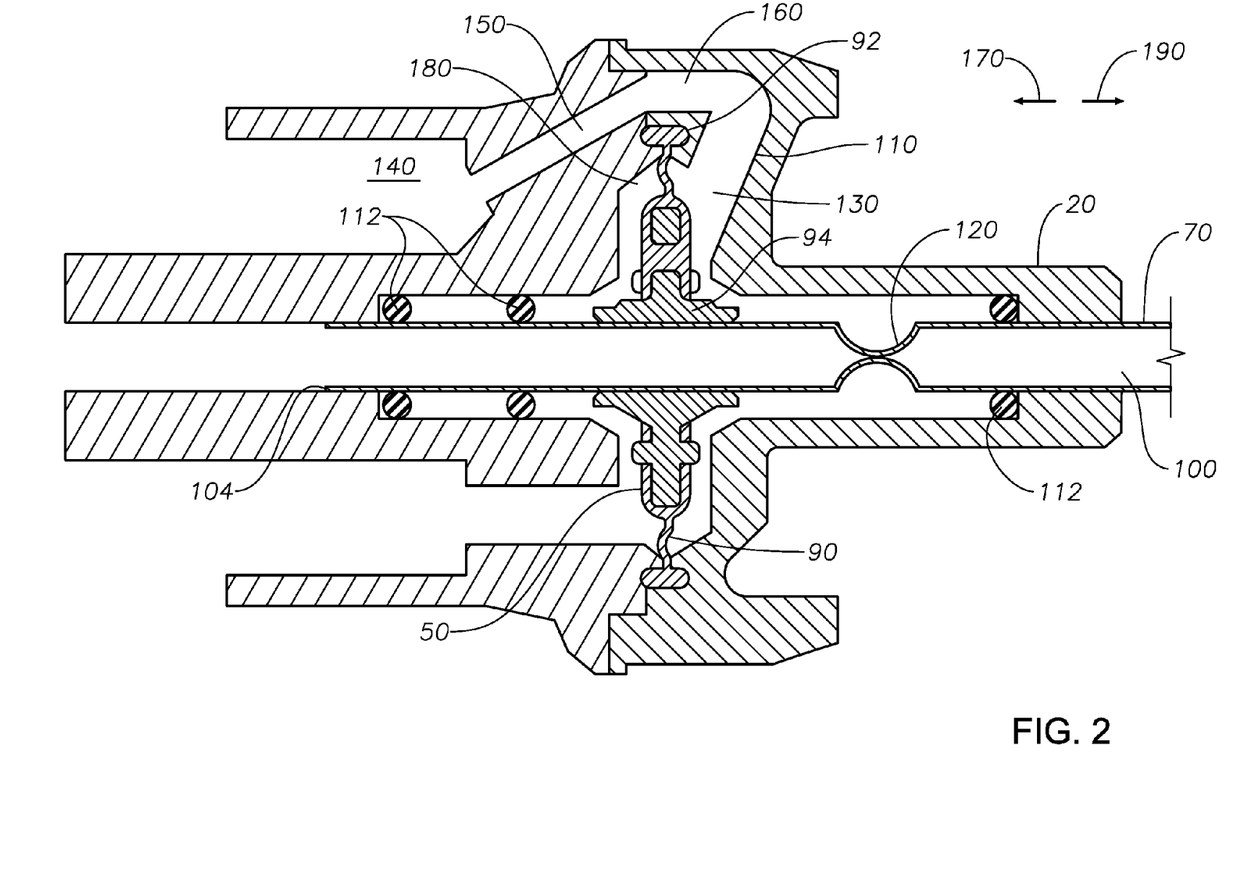
FIG. 2 is a detail view, in schematic form, of a portion of the example vitrectomy probe shown in FIG. 1.

FIG. 2 is a detail view, in schematic form, of a portion of the example vitrectomy probe 10. In this example, the inner cutting assembly 70 includes a valve 120. The valve 120 is operable to form a barrier or closure in the passageway 100. In some instances, the barrier may be a fluid-tight barrier that prevents passage of fluid. In other instances the barrier may not be fluid-tight. In some instances, the valve 120 may be a pinch valve. For example, in some instances, the valve 120 may be a pneumatic pinch valve. Thus, valve 120 may operate in response to pneumatic pressure to open or close or constrict a portion of the passageway 100. The valve 120 may actuate at a selected pressure.

Other types of valves may be utilized. For example, in other instances, the valve 120 may be an electric, hydraulic, or any other suitable type of valve or device that is selectively operable to form a barrier in the passageway 100. Therefore, it is within the scope of the disclosure to encompass any device or feature that is selectively operable to open and close the passageway 100.

In the example shown, the valve 120 is a pneumatic pinch valve that is actuated in response to pneumatic pressure applied to chamber 110. Thus, in the example shown, the valve 120 actuates in response to the pneumatic pressure used to actuate diaphragm 90. In other instances, pneumatic pressure used to actuate valve 120 may be different from pneumatic pressure used to actuate the diaphragm 90. Still further, in some instances, pneumatic pressure applied to the valve 120 may be applied solely for the purpose of actuating the valve 120 or otherwise independently of actuation of the motor 50.

As shown in FIG. 2, pneumatic pressure is applied to a first portion 130 of chamber 110 via passageways 140, 150, and 160. In FIG. 2, the applied pneumatic pressure is at or above a pressure needed to close the valve 120, as illustrated. The pneumatic pressure may also be operable to displace the diaphragm 90 of motor 50 and the inner cutting assembly 70 in the direction of arrow 170. With the valve 120 in the closed configuration, as the inner cutting assembly 70 is displaced in the direction of arrow 170, a piston effect drives flow in the passageway 100. As a result, materials, such as fluids and tissues, are drawn through the port 32 and into the lumen 60 of the outer cutting member 30. The valve 120 returns to an open configuration upon removal of the pneumatic pressure from the first portion 130 of chamber 110. Upon application of pneumatic pressure to a second portion 180 of the chamber 110, the diaphragm 90 and inner cutting assembly 70 are displaced in the direction of arrow 190. However, it is believed that materials drawn into the passageway 100 substantially remain in a position relative to the housing and are not carried along with the inner cutting assembly 70 in any significant degree. Thus, cycling of the diaphragm 90 and inner cutting assembly 70 not only results in a cutting action of materials entering the port 32 but also in the net movement of materials through the lumen 60 and passageway 100.

Figure 3A:
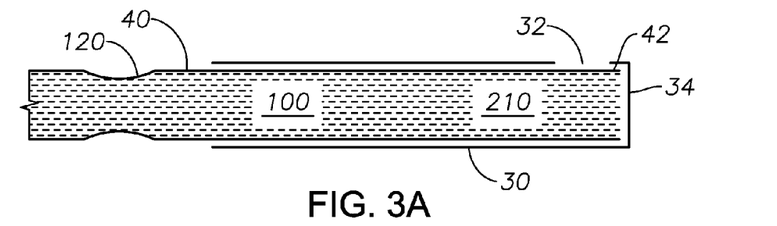
FIGS. 3A-3E shows schematic views of the operation of an example cutting mechanism that includes a valve selectively moveable into an open configuration and a closed configuration.
Figure 3B:
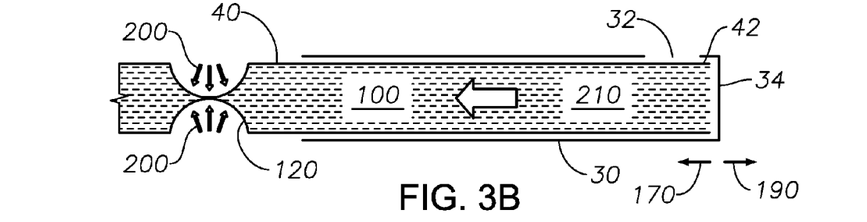
Figure 3C:
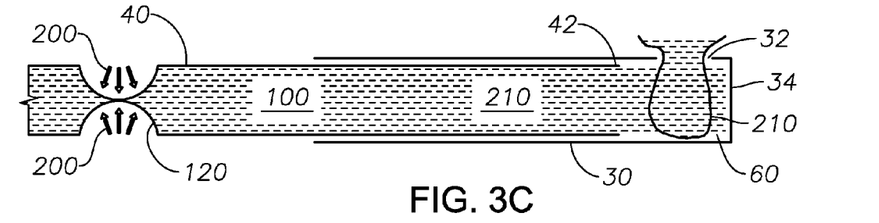

FIGS. 3A-3E are schematic views of the outer cutting member 30, the inner cutting member 40, and the valve 120 that illustrate the cutting and aspiration action. FIG. 3A shows the inner cutting member 40 in a fully extended position such that port 32 is closed. In FIG. 3B, pneumatic pressure 200 is applied to valve 120 resulting in valve 120 being placed into the closed configuration. As shown, the closed configuration of valve 120 forms a closure in the passageway 100. The closure may be fluid-tight. In FIG. 3C, the inner cutting member is displaced in the direction of arrow 170. In some instances, displacement of the inner cutting member 40 in the direction of arrow 170 may be the result of the pneumatic pressure 200 applied to a diaphragm, such as diaphragm 90. In other instances, the pneumatic pressure may not be utilized to actuate the motor, such as motor 50. As the inner cutting member 40 is displaced in the direction of arrow 170, the material contained in passageway 100 is moved along with the inner cutting member 40. Generally, the materials contained in the passageway 100 are incompressible (e.g., liquids and tissues), and retraction of the inner cutting member 40 in the direction of arrow 170 generates movement of the material in passageway 100 in a manner similar to the way in which a fluid-filled straw retains the fluid as the straw is withdrawn from the source of fluid. That is, as the inner cutting member 40 is retracted in the direction of arrow 170, the material within the passageway 100 is retained as a result of fluid continuity and conservation of mass.

Furthermore, as the inner cutting member 40 is displaced in the direction of arrow 170, the size of the passageway 100 between the valve 120 and the distal end 34 of outer cutting member 30 increases. As a result of this increase in volume of passageway 100, additional material enters the outer cutter member 30 through port 32 according to the same physical principles, i.e., fluid continuity and conservation of mass. Thus, the motion of the inner cutting member 40 in the direction of arrow 170 causes materials, for example vitreous humor, fluid, and other ocular tissues, (referred to collectively hereinafter as "vitreous 210") to enter into outer cutting member 30 via port 32, as shown in FIG. 3C.

Figure 3D:
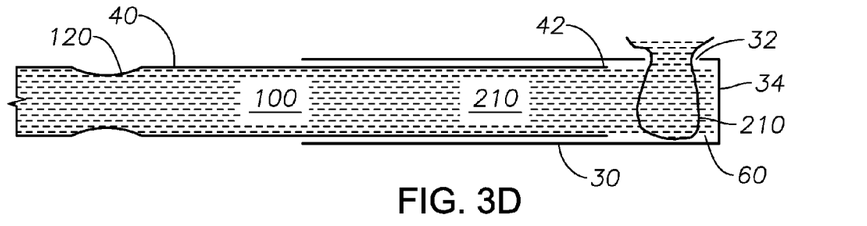

In FIG. 3D, the pneumatic pressure 200 applied to valve 120 is removed or reduced below a level required to actuate the valve 120 into the closed configuration. As a result, the valve 120 is actuated into the open configuration such that passageway 100 is no longer obstructed. The pressure at which the valve 120 opens and closes and time to actuate the valve 120 between the open configuration and closed configuration may be selected so that the valve 120 fully or substantially fully closes before or substantially simultaneous with movement of the inner cutting member 40 in the direction of arrow 170 or opens before or substantially simultaneous with movement of the inner cutting member 40 in the direction of arrow 190. With the valve 120 open the material contained within the passageway 100 is believed to substantially remain in place as the inner cutting member 40 is displaced in the direction of arrow 190.

Figure 3E:
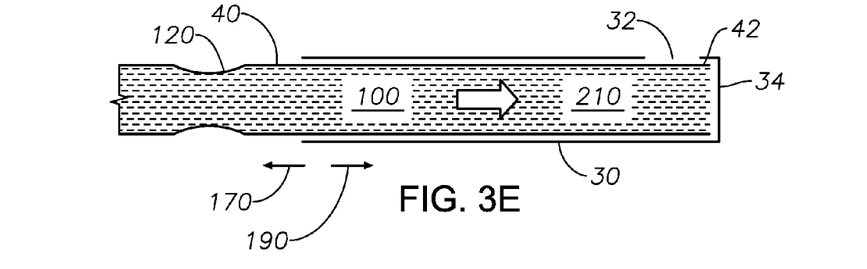

In FIG. 3E, the inner cutting member 40 is displaced in the direction of arrow 190, causing a distal end 42 of the inner cutting member 40 to sever the vitreous 210 extending through port 32. As the cutting and aspiration action illustrated in FIGS. 3A-3E is repeated, application of pneumatic pressure 200 to valve 120 and displacement of the inner cutting member 40 in the direction of arrow 170 results in a step-wise movement of the severed vitreous 210 in the direction of arrow 170 and ultimately out of the vitreoretinal probe.

Consequently, closure of valve 120 and retraction of inner cutting member 40 in the direction of arrow 170 results in step-wise or incremental movement of severed materials. This manner of pumping material eliminates the need for a downstream vacuum source to draw the severed materials out of the vitreoretinal probe 10. Further, with the movement of material in this incremental way, the amount of vitreous 200 entering the probe 10 is better controlled as compared to a constantly applied vacuum. This control of the amount of vitreous 210 drawn into the port may eliminate or substantially reduce traction on the retina.

A constant vacuum applied during a vitrectomy procedure may result in a large an amount of vitreous being drawn into the port of the cutter before the inner cutting member has cut the ingested vitreous. The amount of vitreous drawn into the probe is a function of the strength of the applied vacuum and the time the cutter port remains open. The larger amount of vitreous drawn into the probe generally results in a larger amount of traction that may be applied to the retina. This traction on the retina can result in a retinal tear or otherwise damage the retina.

With the displacement pumping action described herein, the amount of vitreous drawn into the outer cutting member per each cutting cycle is controlled. For example, the amount of vitreous drawn into port 32 of the cutter 25 may be controlled by the length of the stroke of the inner cutting member 40 between its fully retracted position and its fully extended position. A longer stroke may result in a larger amount of vitreous being drawn into the vitreoretinal probe 10, while a shorter stroke may correspond to smaller amount of vitreous being drawn into the vitreoretinal probe 10. In some examples, the vitreoretinal probe 10 may include features to adjust the stroke length such that vitreous flow rate can be controlled. Traction applied to the retina is relieved by each cutting event. Therefore, a shorter stroke length results in smaller amounts of vitreous ingested into the vitreoretinal probe 10 between cutting events and, thus, less traction develops between cutting events.

With the described displacement pumping, the amount of vitreous drawn into port 32 of the cutter 25 is approximately the same per each cutting cycle, independent of the cycle rate of the probe. Thus, the removal rate of vitreous can be controlled by changing the cycle rate of the cutter of the vitreoretinal probe. Moreover, the vitreous removal rate can be changed without increasing the amount of retinal traction. In fact, it is believed that by utilizing this type of displacement pumping, retinal traction may be substantially reduced or eliminated independently of the cycle rate of vitreoretinal probe cutter. For example, increasing the cycle rate of a vitreoretinal probe that utilizes the pumping action described may result in a one-to-one increase in vitreous removal rate. However, any retinal traction may be unchanged because, as explained herein, retinal traction is independent of cycle rate. Rather, it is stroke length that may have an effect on retinal traction. Thus, the material removal rate is dependent on cycle rate, and the amount of traction produced is believed to be independent of both cycle rate and material removal rate. Consequently, with controlled displacement pumping, as described herein, traction applied to the retina of an eye during a vitrectomy may be significantly reduced.

Although the example illustrated in FIGS. 3A-3E is described in the context of a pneumatically-actuated valve, the scope of the disclosure is not so limited. Rather, the valve may be actuated in any manner to form a closure in the aspiration passageway, such as passageway 100. Therefore, the example illustrated in FIGS. 3A-3E is provided as a non-limiting example.

In implementations in which actuation of the valve 120 is independent of the actuation of the motor 50, opening and closing of the valve 120 may be timed relative to movement of the inner cutting assembly 70. For example, with the inner cutting assembly 70 in a fully extended position, the valve 120 may be closed before the inner cutting assembly 70 begins retraction in the direction of arrow 170. This sequence ensures formation of a closure in the inner cutting assembly 70 before the inner cutting assembly 70 is retracted in the direction of arrow 170. The valve 120 may then be opened before the inner cutting assembly 70 begins extension in the direction of arrow 190, providing an unobstructed passageway 100 so that movement of the inner cutting assembly 70 in the direction of arrow 190 minimizes or eliminates movement of the aspirated material within the passageway 100 in the direction of arrow 190.

Figure 4:
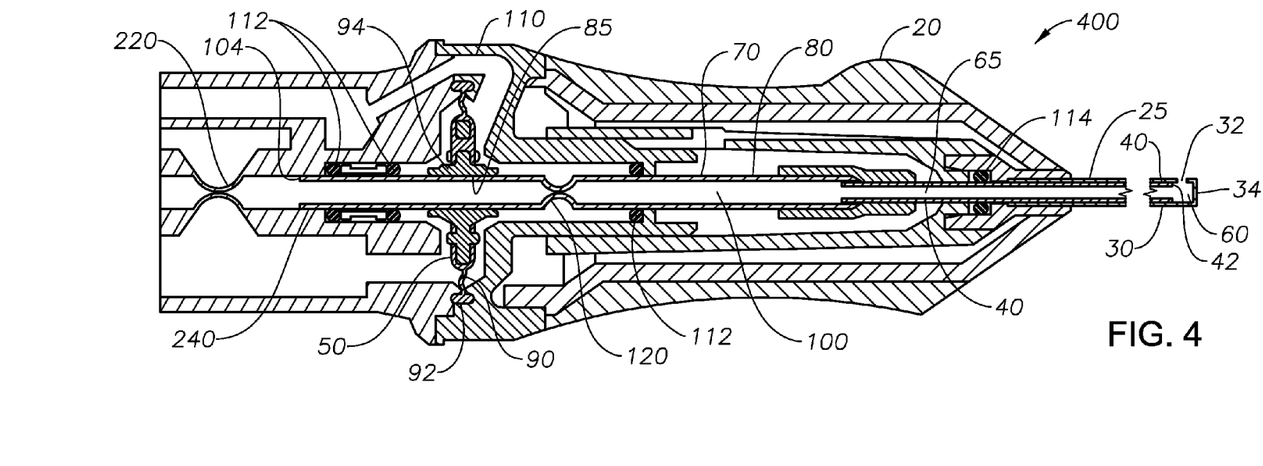
FIG. 4 is a cross-sectional view of another example vitrectomy probe.
Figure 5:
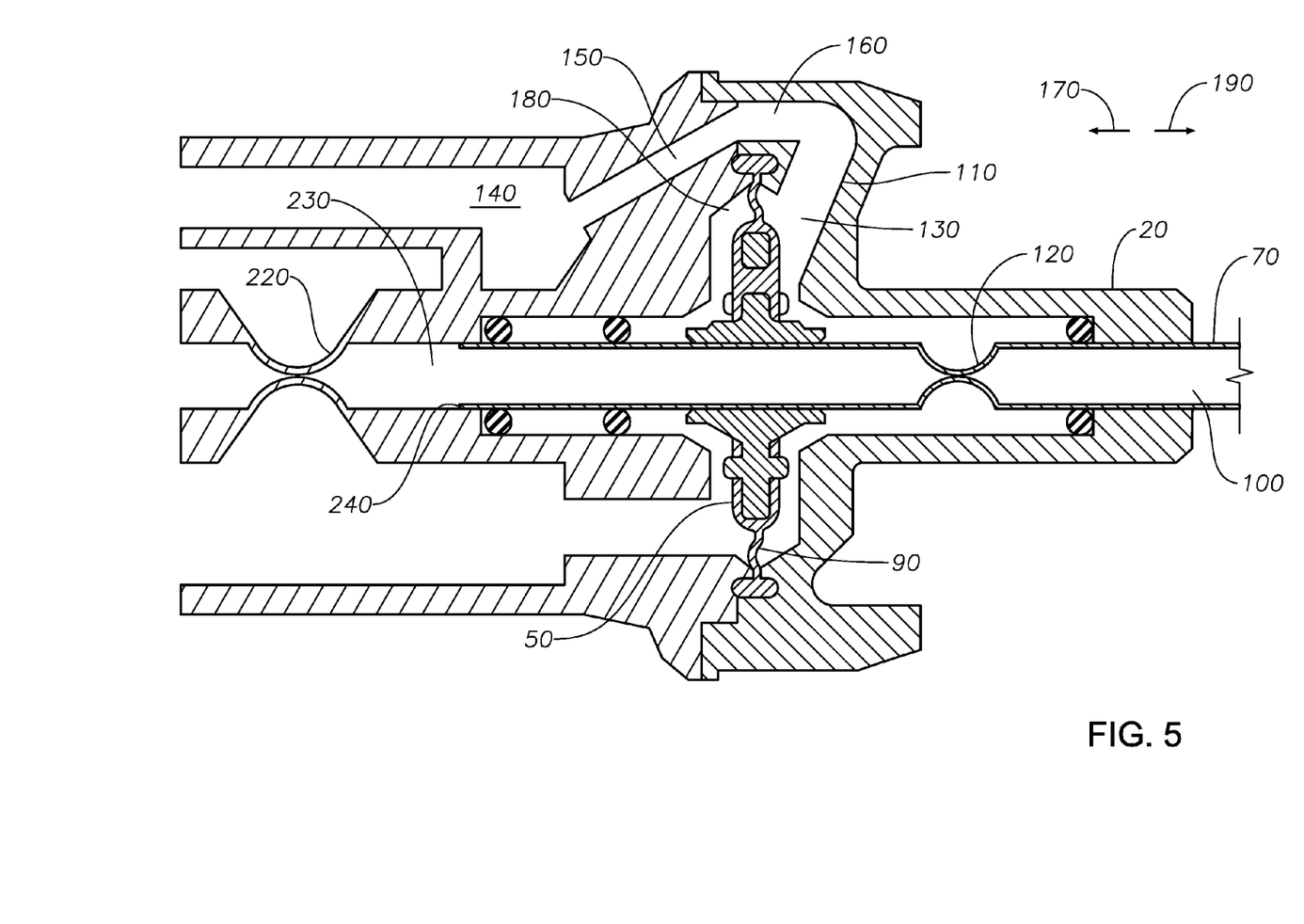
FIG. 5 is a detail view, in schematic form, of a portion of the example vitrectomy probe shown in FIG. 4.

FIG. 4 shows a cross-sectional view of another example vitrectomy probe 400. FIG. 5 is a detail view of a portion of vitrectomy probe 400. This example vitrectomy probe 400 may be similar to the vitrectomy probe 10, discussed above. However, as shown in FIG. 5, the vitrectomy probe 400 includes a second valve 220. In the illustrated example, the second valve 220 is a pneumatically-actuated pinch valve. However, the scope of the disclosure is not so limited. Rather, the second valve 220 may be an electric, hydraulic, or any other suitable type of valve or device that is selectively operable to form a barrier.

As shown in FIG. 5, the second valve 220 is disposed in a passage 230 formed in the housing 20 of the example vitrectomy probe 400. The passage 230 may be sized such that proximal end 240 of the inner cutting assembly 70 is received and permitted to move axially therein. The second valve 220 may be actuated by pneumatic pressure applied to displace the diaphragm 90 and inner cutting assembly 70 in the direction of arrow 190. In the illustrated example, pneumatic pressure applied to second portion 180 of chamber 110 is operable to displace diaphragm 90 and inner cutting assembly 70 in the direction of arrow 190 and cause the second valve 220 to close.

The second valve 220 may be actuated at a selected pressure. For example, the pneumatic pressure at which the second valve 220 moves between an open configuration and a closed configuration may be different than the pneumatic pressure needed to displace diaphragm 90 within the chamber 110. In some instances, the second valve 220 may actuate a pneumatic pressure lower than the pneumatic pressure at which the diaphragm 90 actuates in the direction of arrow 190. In other instances, the second valve 220 and diaphragm 90 may be actuated at the same pneumatic pressure.

The second valve 220 may be used in cooperation with valve 120. For example, with the inner cutting assembly 70 fully retracted in the direction of arrow 170, pneumatic pressure may be applied to a second portion 180 of chamber 110 after the pneumatic pressure applied to the first portion 130 of chamber 110 has been removed. This change in pressure states results in the valve 120 being placed in an open configuration and the second valve 220 being placed in a closed configuration. With the valves 120, 220 in these configurations, as the inner cutting assembly 70 moves in the direction of arrow 190, the closed valve 220 maintains the position of the vitreous presently within the passageway 230 and passageway 100 in the same manner described above. That is, the position of the vitreous is maintained as a result of conservation of mass that prevents the vitreous from moving away from the closed valve 220. Consequently, the vitreous contained in the passageway 100 is prevented from moving in the direction of arrow 190. Thus, when closed, the second valve 220 prevents expulsion of vitreous out of the port 32 before the inner cutting member 40 had performed a cut. When the pressure conditions change such that pneumatic pressure is released from the second portion 180 of chamber 110 and pneumatic pressure is added to the first portion 130 of chamber 110, the configurations of the first and second valves 120, 220 reverse. That is, the first valve 120 closes, and the second valve 220 opens. As already explained, in some implementations, the second valve 220 may be eliminated.

Figure 6A:
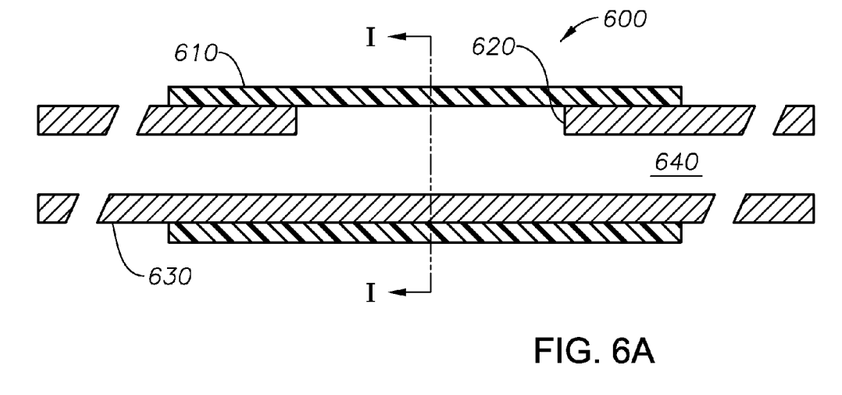
FIGS. 6A and 6B show cross-sectional views of a valve along a longitudinal axis in an open configuration and a closed configuration, respectively.
Figure 6B:
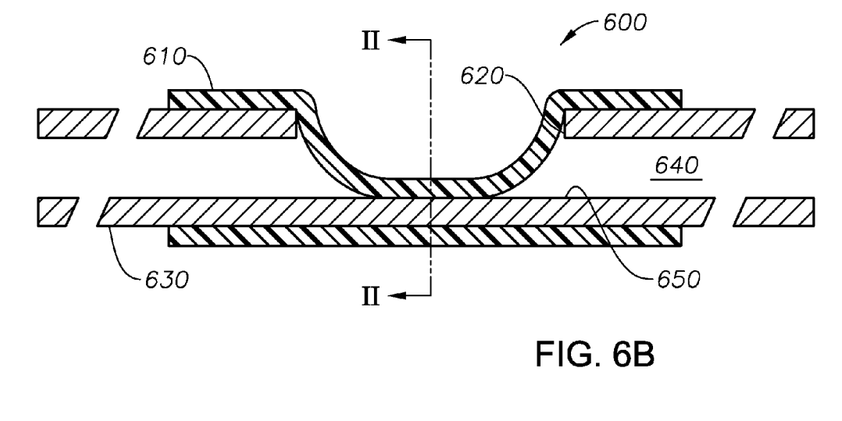

FIGS. 6A and 6B show an example valve 600 that is within the scope of the present disclosure. Valve 600 includes a resilient member 610 that may be received over an opening 620 formed in a tubular member 630. In some implementations, the resilient member 610 may be in the form of a tube formed of a flexible material. In some instances, this type of valve may be used for valve 120 or valve 220 or both. In FIG. 6A, the valve is in an open configuration, such that the passageway 640 is unobstructed. In FIG. 6B, the valve 600 is in a closed configuration forming an obstruction in the passageway 640.

In some instances, the resilient member 610 may be elastomeric. For example, the resilient member 610 may be formed from a rubber material. Any other material that includes a bias to return the material to its original state may also be used. In some implementations, the resilient material 610 may include electromagnetic particles that allow the resilient material 610 to be influenced by applied electromagnetic forces. In some implementations, the resilient material 610 may possess piezoelectric or other properties that enable its shape or position to be influenced by means other than by application of pressure. In some instances, the tubular member 630 may be formed from a metal, plastic material, or any desired material.

In the open configuration shown in FIG. 6A, no force is being applied to the resilient member 610. The resilient member 610 maintains its cylindrical shape. Consequently, the passageway 640 remains unobstructed. In some implementations, the resilient member 610 may have such resilience that it maintains a generally cylindrical shape even when a selected amount of pressure difference is present between the exterior of the valve 600 and the passageway 640. Above the selected pressure differential, the resilient member 610 may deform and form an obstruction. Thus, in use, aspirated materials may be transported through the passageway 640 even when a pressure differential below the selected pressure differential is present. For example, in some implementations, the resilient member 610 may remain unobstructed notwithstanding application of vacuum to the interior of the passageway 640 by a downstream vacuum source where the applied vacuum is below the selected pressure differential. In the closed configuration, shown in FIG. 6B, a portion of the resilient member 610 is displaced into the passageway 640 through the opening 620 and contacts an interior surface 650 of the passageway 640 to form a seal. The formed seal may be an air-tight seal. In some instances, the resilient member 610 may be responsive to pneumatic pressure to actuate the valve 600 between the open and closed configurations. Thus, in some implementations, the resilient member 610 may react to a pressure differential between the exterior of the valve 600 and the passageway 640 to open and close the valve 600. The pressure differential at which the valve 600 opens and closes may be selected as desired. The selected pressure differential at which the valve 600 opens and closes may be such that a vacuum below a selected pressure differential may be applied to the passageway 640 to aspirate material therethrough without causing the valve 600 to close.

Figure 6C:
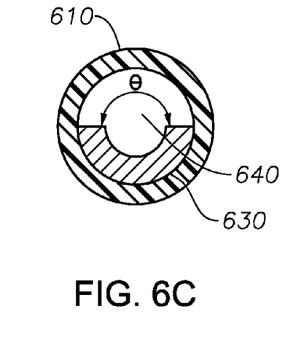
FIGS. 6C and 6D are transverse cross-sectional views of the example valve shown in FIGS. 6A and 6B in the open configuration and the closed configuration, respectively.
Figure 6D:
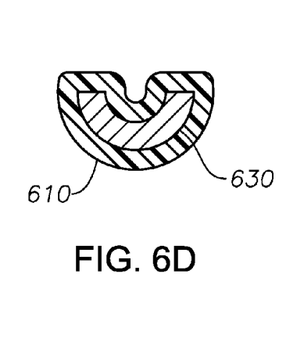

In other implementations, a physical member may be applied to the resilient member 610 to force a portion of the resilient member 610 through the opening 620. In other implementations, the resilient member 610 may be actuated hydraulically, electromagnetically, piezoelectrically, thermopneumatically, or in any other fashion. FIG. 6C is a cross-sectional view of valve 600 taken along I-I showing the passageway 640 in an open, unobstructed condition. FIG. 6D, on the other hand, is a cross-sectional view of valve 600 taken along II-II showing the passageway 640 in a closed condition.

The material forming the resilient member 610 may be selected such that the material reacts quickly to an applied closing force. That is, once a force applied to the resilient member 610, whether pneumatic, hydraulic, electromagnetic, direct contact, or any other manner, that corresponds to the force at which the valve 600 is to close, the material forming the resilient member 610 may be selected to react quickly to fully close the valve. Quick reaction by the valve to open and close relative to the motion of the inner cutting assembly 70 is desirable to promote efficiency of the incremental pumping mechanism.

Although FIGS. 6A-6D show the resilient member 610 forming a tubular member surrounding a portion of the tubular member 630, in other implementations, the resilient member 610 may be a not be in the form of a tube. For example, in some instances, the resilient member may have a size only large enough to cover the opening 620 in the tubular member 630. In other instances, the resilient member 620 may be an insert received into the opening 620.

Although the example valve 600 is shown as having a circular cross-section, the scope of the disclosure is not so limited. Rather, the valve 600 may have any cross-sectional shape. Also, referring to FIGS. 6C and 6D, the opening 620 has an angular component, $\theta$, that is approximately 180°. However, the angular size of the opening 620 may be greater or less than 180°.

Although the disclosure provides numerous examples, the scope of the present disclosure is not so limited. Rather, a wide range of modification, change, and substitution is contemplated in the foregoing disclosure. It is understood that such variations may be made to the foregoing without departing from the scope of the present disclosure.

What is claimed is:

1. A vitrectomy probe comprising:
   a body;
   a cutter extending from the body, the cutter comprising:
      an outer cutter portion; and
      an inner cutter portion slideable within the outer cutter portion between an extended position and a retracted position;
   a diaphragm coupled to the inner cutter portion and disposed within a chamber formed in the body and dividing the chamber into a first chamber portion and a second chamber portion, the diaphragm moveable in a first direction to retract the inner cutter portion in response to a first pneumatic pressure introduced into the first chamber portion; and
   a first valve coupled to the inner cutter portion, at least a portion of the valve disposed in the first chamber portion and adapted to close upon introduction of the first pneumatic pressure into the first chamber portion.

2. The vitrectomy probe of claim 1, further comprising an inner cutting assembly, the inner cutting assembly comprising the inner cutter portion, a tubular member, and the first valve.

3. The vitrectomy probe of claim 2, wherein the inner cutting assembly defines a passageway therethrough.

4. The vitrectomy probe of claim 3, wherein the first valve is operable to form a closure within the passageway.

5. The vitrectomy probe of claim 1 further comprising a second valve disposed in the body adjacent to an end of the inner cutting assembly opposite the inner cutter portion.

6. The vitrectomy probe of claim 5, wherein the second valve is adapted to close upon introduction of a second pneumatic pressure into the second chamber portion.

7. The vitrectomy probe of claim 1, wherein the valve is directly exposed to the first pneumatic pressure and wherein the valve compresses to constrict in response to the first pneumatic pressure.

* * * * *